(12) United States Patent
Zhang

(10) Patent No.: US 7,611,467 B2
(45) Date of Patent: Nov. 3, 2009

(54) METHOD AND APPARATUS FOR EXTRACTING AN ENVELOPE CURVE OF A SPECTROGRAM

(75) Inventor: Yu Zhang, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 561 days.

(21) Appl. No.: 11/316,048

(22) Filed: Dec. 21, 2005

(65) Prior Publication Data

US 2007/0016045 A1  Jan. 18, 2007

(30) Foreign Application Priority Data

Jun. 10, 2005  (CN) .................. 2005 1 0035267

(51) Int. Cl.
 *A61B 5/026* (2006.01)
(52) U.S. Cl. ............... 600/453; 600/454; 600/455; 600/456; 600/457; 73/641
(58) Field of Classification Search .......... 600/453–457
 See application file for complete search history.

(56) References Cited

U.S. PATENT DOCUMENTS

| 5,868,676 | A | * | 2/1999 | McCabe et al. ............. 600/454 |
| 5,935,074 | A | * | 8/1999 | Mo et al. ................... 600/454 |
| 6,050,948 | A |   | 4/2000 | Sasaki et al. |
| 6,663,566 | B2 | * | 12/2003 | Pan et al. .................... 600/454 |

FOREIGN PATENT DOCUMENTS

| EP | 0 381 348 A1 | 8/1990 |
| JP | 3-228751 | 10/1991 |
| JP | 2000-287946 | 10/2000 |
| JP | 2005-046194 | 2/2005 |

OTHER PUBLICATIONS

Evans, David H., et al., Doppler Ultrasound: Physics, Instrumentation and Signal Processing. pp. 179-184. 2nd Edition, John Wiley & Sons Inc. 2000.

(Continued)

*Primary Examiner*—Long V Le
*Assistant Examiner*—Vani Gupta
(74) *Attorney, Agent, or Firm*—Kory D. Christensen; Stoel Rives LLP

(57) ABSTRACT

A method and apparatus for extracting an envelope curve of a spectrogram, for use in measurement of blood flow velocity by using spectral Doppler techniques, the method comprising steps of: processing RF ultrasound echo signals to obtain Doppler signals; performing spectral analysis on the Doppler signals, to obtain a corresponding power spectrum P(f); estimating a forward maximum frequency $f_{max+}$ and a backward maximum frequency $f_{max-}$ for the Doppler signals at a predetermined moment, according to the power spectrum P(f) of the Doppler signals at the predetermined moment; determining a noise frequency range according to the two maximum frequencies, so as to estimate an average noise power E; and correcting the forward maximum frequency and the backward maximum frequency by using the average noise power E. With the method of the invention, influence from the SNR and bandwidth on the envelope curve may be reduced, so as to be useful for accurate computation of blood flow parameters.

16 Claims, 4 Drawing Sheets

OTHER PUBLICATIONS

Moraes, R., et al., "The Performance of Three Maximum Frequency Envelope Detection Algorithms for Doppler Signals," Journal of Vascular Investigation, Sep. 1995. pp. 126-134. vol. 1, No. 3, Pearson Professional Ltd.

Rickey, D. W., et al., "Evaluation of an Automated Real-Time Spectral Analysis Technique," Ultrasound in Medicine and Biology, 1996. pp. 61-73. vol. 22, No. 1, World Federation for Ultrasound in Medicine & Biology, USA.

Mo, Larry Y. L., et al., "Comparison of Four Digital Maximum Frequency Estimators for Doppler Ultrasound," Ultrasound in Medicine and Biology, 1988. pp. 355-363. vol. 14, No. 5, Pergamon Press plc, USA.

* cited by examiner

METHOD AND APPARATUS FOR EXTRACTING AN ENVELOPE CURVE OF A SPECTROGRAM

FIELD OF THE INVENTION

The invention relates to an ultrasound technique, and more particularly, to an ultrasound technique for measuring the flow velocity of a liquid by using spectral Doppler techniques, especially for extracting an envelope curve of a spectrogram in measurement of blood flow velocity.

BACKGROUND OF THE INVENTION

Ultrasound techniques are widely applied to medical imaging and measurements, where the research or practice of measuring blood flow velocity by using Doppler techniques has been deployed broadly in physics, engineering and clinics. In measurement of blood flow velocity by a continuous wave Doppler system, an ultrasound diagnostic system transmits an ultrasound into a sample volume within the human body, and receives the echoes scattered by the blood cells in the sample volume. Since the motion of the blood cells produces Doppler effect (the scattered echo has a certain frequency shift with respect to the transmitted wave and the shift is proportional to the moving speed of the blood cells), the blood flow condition in the vessels can be estimated by measuring the frequency shift. In measurement of blood flow velocity by a pulsed wave Doppler system, the system transmits pulsed waves repeatedly at certain intervals and receives the scattered echoes at a moment between two consecutive transmissions, and implements measurement of the flow velocity by measuring the change rate of the phase difference between different scattered echoes and a reference signal over time. In principle, measurement of flow velocity by pulsed wave Doppler techniques does not depend on Doppler effect, but the measured relationship between the signal frequency shift and the moving speed of the blood cells accords with Doppler effect. Therefore, processing of pulsed wave Doppler signals is generally similar to that of continuous wave Doppler signals in engineering and clinics.

After quadrature demodulation and filtering are performed on an RF ultrasound scattered echo signal, the spectrum of the Doppler signal is moved from several MHz to the audio range with bandwidth of several KHz centered at zero frequency (the signals thus formed in the range is generally referred to as audio Doppler signals, and termed as Doppler signals, for ease of illustration hereafter). Due to the viscosity of blood, blood flow velocity has a certain distribution within the vessels in the human body, being about 0 near the vessel walls and larger near the center of the vessels, and accordingly the spectrum of the Doppler signals has a width, where the maximum frequency is proportional to the maximum blood flow velocity in the vessels. Furthermore, the blood flow velocity within a vessel varies constantly with contraction and relaxation of the heart, so the spectrum of the Doppler signals detected varies constantly. Taking the Doppler signals at a particular moment for spectral analysis, we can estimate the blood flow condition in the vessels at this moment. If Doppler signals are taken at certain intervals for spectral analysis and the power of components with different frequencies is modulated with gray levels and displayed in order of time, the spectrogram of the Doppler signals can be obtained.

To diagnose disease of blood vessels by using the spectrogram for Doppler signals, some parameters are required to be extracted from the spectrogram, such as the average flow velocity, maximum flow velocity, minimum flow velocity, S/D (ratio of the maximum flow velocity during systole and that at the end of diastole), RI (resistive index), PI (pulsatility index) and so on. All of these parameters can be computed based on the envelope curve or average frequency curve for the spectrogram. The envelope curve for the spectrogram may be obtained by connecting the maximum frequencies of the Doppler signal spectrum at different moments, the amplitude of the envelope curve being proportional to the maximum blood flow velocity in the vessels. The maximum frequency is the basis for estimation. of the average frequency and computation of other Doppler parameters, and accordingly it is of great significance to estimate the maximum frequency accurately in clinical applications.

Conventional methods for estimating the maximum frequency is characterized in that, after an operator of a Doppler system determines that the spectrogram in the display meets the required characteristics, the spectrogram is frozen, the maximum frequency curve is manually plotted and then the average frequency or its associated parameters are automatically computed by some software tools. Its obvious disadvantage lies in poor repetition, low estimation accuracy and inability for real-time estimation. Due to influences from pulsate of the arterial blood flow and various noises, it has been very hard to estimate the maximum frequency in applications of spectral Doppler techniques. With rapid development of digital computing techniques, researchers have proposed many methods for estimating the maximum frequency, including PM (Percentile method), TCM (Threshold-crossing method), MTCM (modified threshold-crossing method), HM (Hybrid method), GM (Geometric method), MGM (Modified geometric method), ATM (Adaptive threshold method) and etc. These methods are generally used for spectrum estimation systems based on FFT (Fast Fourier Transformation), and alternatively may be used for other spectrum estimation systems. The above methods are explained and compared in Evans et al, Doppler Ultrasound: Physics, Instrumentation and Signal Processing. 2rd Edition, Chichester, UK: John Wiley & Sons Inc; 2000. The PM approach has a small computation amount but is subject to the influence from the SNR and bandwidth. In methods such as TCM, due to the presence of random noises whose spectral amplitude varies greatly, noise components with larger amplitude will easily be detected to lead to overestimation of the maximum frequency if the threshold is set too small. On the other hand, estimation of the maximum frequency tends to be small if the threshold is set too large (for details, please see "Comparison of four digital maximum frequency estimators for Doppler ultrasound", Ultrasound Med Biol, Vol. 14, No. 5, pp 355-363, 1998). Some ATMs are proposed for use in existing commercial ultrasound imaging systems by Routh et al in U.S. Pat. No. 5,287,753 and "Evaluation of an automated real-time spectral analysis technique" (for details, please see Ultrasound Med Biol, Vol. 1, No. 1, pp 61-73) and Mo in U.S. Pat. No. 5,935,074, but the threshold has to be set larger in practice in order to increase the robustness for estimation of the maximum frequency. In ATM, the threshold value is set according to the SNR of the signals. Due to overlap of signals and noises in some spectrum, it will bring large errors and variances to estimation of SNR if signals and noises are discriminated by using threshold only, and thus accuracy and robustness for estimation of the maximum frequency are affected. GM has no problem in selection of threshold values and can implement automatic extraction of the maximum frequencies. But it takes the position of the selected peak of the power spectrum as the reference, and estimation of the spectrum by FFT has a large variance and the peak position tends to be random to a great extent, so it will affect the accuracy for estimation of the maximum frequency. MGM subtracts the line connecting the maximum point and the minimum point of the curve directly from the integral power spectrum curve, and the position of the maximum in the curve is estimated as the maximum frequency. Compared with others, this method has better robustness (for details, please see "The performance of three maximum frequency envelope detection algorithms for Doppler signals", J Vasc Invest, Vol. 1, pp 126-134). But experiments show that this method also has the problem in underestimation of the maximum frequency when the signal spectrum is relatively wide.

FIG. 1 is a flowchart showing the typical processing of Doppler signals. First, the echo signals received by the ultrasound probe are beam formed, demodulated, filtered and AD (Analog-to-Digital) converted to obtain digital Doppler signals and then spectral analysis is performed on the Doppler signals by using FFT or the like to obtain a spectrogram. Next, the technique such as MGM, ATM or the like is applied to the spectrogram to estimate the maximum frequency of the Doppler signals, so as to extract the envelope curve of the spectrogram. Finally, the Doppler parameters for representing the Doppler signals are calculated according to the characteristic points on the envelope curve.

The above prior arts have a main disadvantage in that the maximum frequency tends to be underestimated, particularly when the spectrum is relatively wide. Further, TCM has a disadvantage in that setting of threshold parameters has too much influence on estimation of the frequency, which causes the computation results of the Doppler parameters to be less accurate.

SUMMARY OF THE INVENTION

In view of the above disadvantages, an object of the invention is to provide a method and apparatus, which may extract an envelope curve of a spectrogram for Doppler signals precisely, to reduce influence from the SNR and bandwidth of the signals, and thus is useful for accurate computation of blood flow parameters.

To fulfill the above object, the invention is based on an idea to combine the initial estimation and correction together. First, an initial estimation of the forward maximum frequency and backward maximum frequency for a power spectrum is performed by using existing techniques, and then the average noise power is determined accurately according to the initially estimated frequency range (by using noise points as many as possible). The average noise power may be used to correct the power spectrum curve and obtain the more accurate corrected forward maximum frequency and backward maximum frequency. Furthermore, the ultimate maximum frequency may be determined by using the direction of the average flow velocity or integration values of the forward and backward blood flow power spectrum, and accordingly the system has increased robustness.

As a solution based on the idea of the invention, an object of the invention is to provide a method for extracting an envelope curve of a spectrogram, for use in measurement of blood flow velocity by using spectral Doppler techniques, comprising steps of:

A. processing RF ultrasound echo signals to obtain Doppler signals;

B. performing spectral analysis on the Doppler signals, to obtain power spectrum P(f) of the Doppler signals which varies over time;

C. estimating a forward maximum frequency $f_{max+}$ and a backward maximum frequency $f_{max-}$ for the Doppler signals at a predetermined moment, according to the power spectrum P(f) of the Doppler signals at the predetermined moment;

characterized in further comprising steps of:

D. determining a noise frequency range according to the forward maximum frequency and the backward maximum frequency, and estimating an average noise power E within the noise frequency range; and E. correcting the forward maximum frequency and the backward maximum frequency by using the average noise power E to obtain the corrected forward maximum frequency $F_{max+}$ and the corrected backward maximum frequency $F_{max-}$.

In the above solution, the noise frequency range is a function of the forward maximum frequency and the backward maximum frequency, represented as $[f_0, F(f_{max-})]+[F(f_{max+}), f_1]$, where $F(f_{max-})$ is a function of variable $f_{max-}$, $F(f_{max+})$ is a function of variable $f_{max+}$ and $[f_0, f_1]$ is the frequency range of the power spectrum P(f).

In the above solution, the step E further comprises steps of:

a. setting a threshold Th(E) according to the average noise power E and previous average noise powers E at previous moments;

b. subtracting the threshold from the power spectrum P(f) of the Doppler signals at the predetermined moment to get a difference function P(f)-Th(E); and c. integrating the difference function to get a function $\phi''(f)$ and obtaining a maximum value and a minimum value of the function $\phi''(f)$, wherein positions of the maximum value and the minimum value corresponding to the corrected forward maximum frequency $F_{max+}$ and the corrected backward maximum frequency $F_{max-}$, respectively.

In the above solution, the step E is followed by the step of:

F. determining one of the corrected forward maximum frequency $F_{max+}$ and the corrected backward maximum frequency $F_{max-}$ as the maximum frequency according to the direction of the blood flow velocity.

In the above solution, an average frequency is estimated according to the power spectrum components between the corrected forward maximum frequency $F_{max+}$ and the corrected backward maximum frequency $F_{max-}$; the direction of the blood flow velocity corresponding to the average frequency is determined; and one of the corrected forward maximum frequency $F_{max+}$ and the corrected backward maximum frequency $F_{max-}$ is determined as the maximum frequency according to the determined direction of the blood flow velocity.

The invention further provides an apparatus for extracting an envelope curve of a spectrogram, for use in measurement of blood flow velocity by using spectral Doppler techniques, the apparatus comprising:

A processing unit, for processing RF ultrasound echo signals to obtain Doppler signals;

An analyzing unit, for performing spectral analysis on the Doppler signals, to obtain power spectrum P(f) of the Doppler signals which varies over time;

A frequency estimation unit, for estimating a forward maximum frequency $f_{max+}$ and a backward maximum frequency $f_{max-}$ for the Doppler signals at a predetermined moment, according to the power spectrum P(f) of the Doppler signals at the predetermined moment;

A noise estimation unit, for determining a noise frequency range according to the forward maximum frequency and the backward maximum frequency, and estimating average noise power E within the noise frequency range; and A correcting unit, for correcting the forward maximum frequency and the backward maximum frequency by using the average noise power E to obtain the corrected forward maximum frequency $F_{max+}$ and the corrected backward maximum frequency $F_{max-}$.

With the above solution, influence from the signal bandwidth and SNR upon the accuracy for estimation of the maximum frequency may be minimized and thus the forward maximum frequency or the backward maximum frequency may be determined and output more easily and accurately, especially when both the forward and backward blood flow is present.

PREFERRED EMBODIMENTS OF THE INVENTION

Detailed descriptions will be given below to the invention with reference to preferred embodiments taken in conjunction with accompanying drawings.

Figure 1:
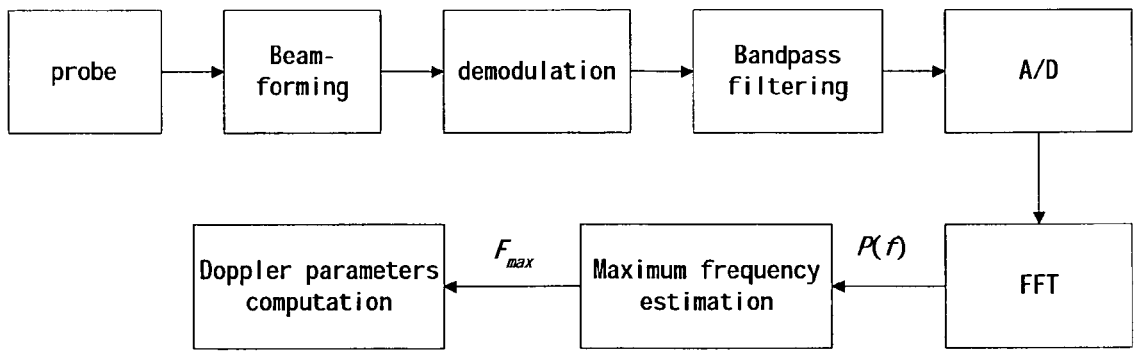
FIG. 1 is a flowchart showing the conventional Doppler signal processing.

The flow for Doppler signal processing in FIG. 1 comprises a method for extracting an envelope curve of a spectrogram, generally comprising steps of:

A. demodulating, filtering and AD converting RF ultrasound echo signals to obtain Doppler signals for a fluid;

B. performing spectral analysis on the Doppler signals, to obtain power spectrum P(f) of the Doppler signals which varies over time; and C. estimating a forward maximum frequency $f_{max+}$ and a backward maximum frequency $f_{max-}$ for the Doppler signals at a predetermined moment, according to the power spectrum P(f) of the Doppler signals at the predetermined moment.

Thus, a system may generate two envelope curves for displaying the spectrogram of the Doppler signals according the maximum frequencies in the power spectrum P(f) of the Doppler signals at different moments, or the system may compute the blood flow parameters directly based on the maximum frequencies at different moments generated with the above steps. The method of the invention makes some improvements to the estimation of the maximum frequencies and the step C is followed by steps of:

D. determining a noise frequency range according to the forward maximum frequency and the backward maximum frequency, and estimating an average noise power E within the noise frequency range; and E. correcting the forward maximum frequency and the backward maximum frequency by using the average noise power E to obtain the corrected forward maximum frequency $F_{max+}$ and the corrected backward maximum frequency $F_{max-}$.

Figure 2:
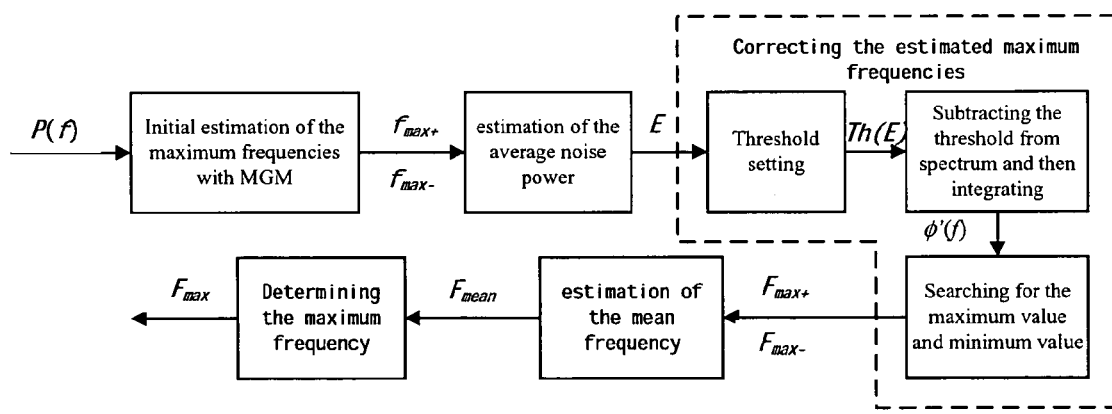
FIG. 2 is a flowchart showing the method for estimating the maximum frequency and the mean frequency according to the invention.

FIG. 2 is a flowchart illustrating the estimation method of the invention. The forward maximum frequency $f_{max+}$ and backward maximum frequency $f_{max-}$ at step C may be estimated initially by using existing techniques. The flowchart comprises, but not limited to, performing an initial estimation of the forward maximum frequency and the backward maximum frequency by using MGM. Similarly, the spectral analysis performed upon the Doppler signals at step B comprises, but not limited to, short-time Fourier transform. The related methods are known and the description thereto is omitted herein.

Figure 3:
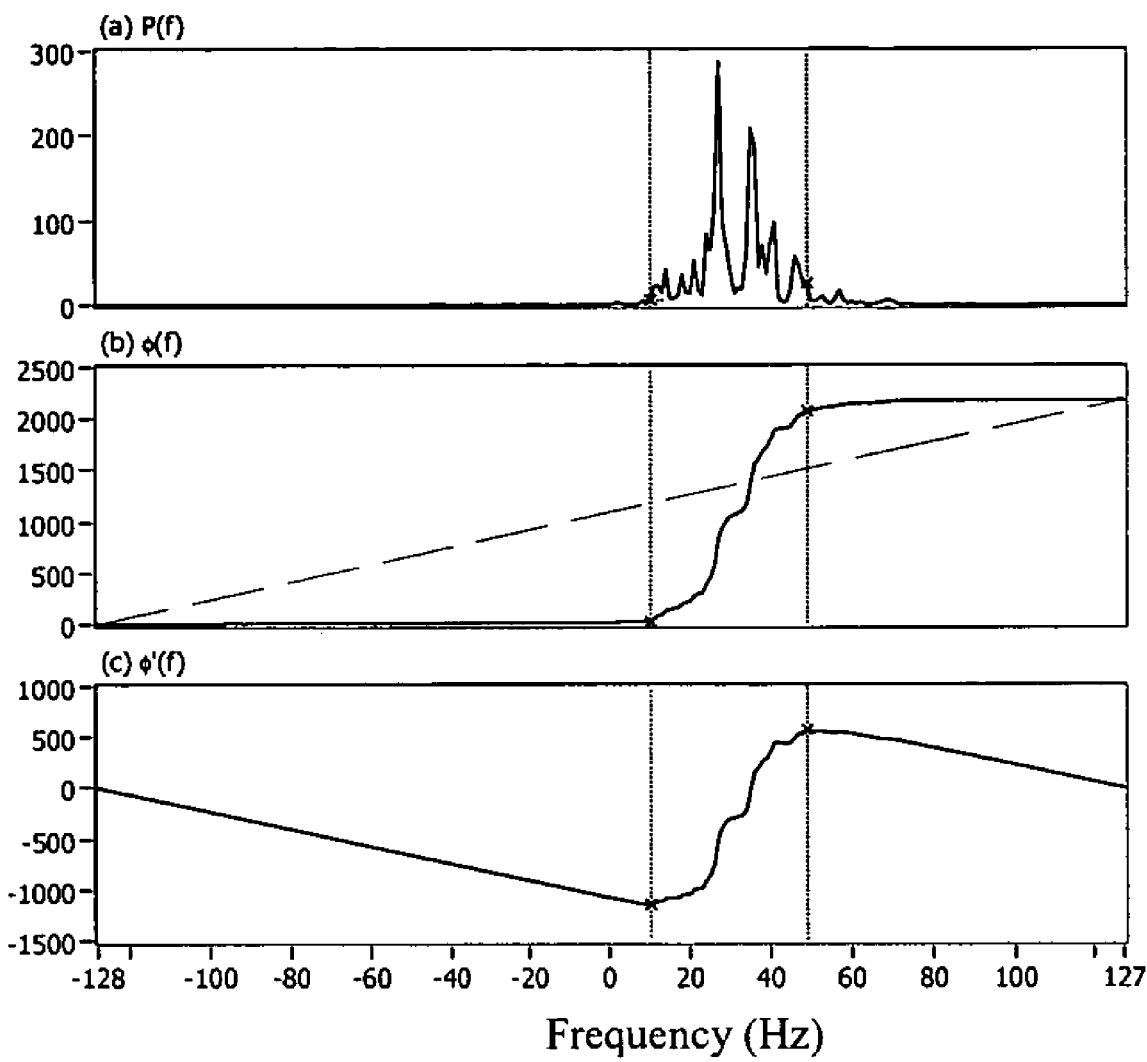
FIG. 3 is a schematic view of extracting the maximum frequency of the Doppler signals with MGM.

FIG. 3 illustrates the signal processing with MGM. Taking the power spectrum function P(f) of the Doppler signals at a predetermined moment shown in FIG. 3(a) as an example, the power spectrum function is integrated from frequency $f_0$ to get a solid curve as shown in FIG. 3(b), which may be given by $$\phi(f) = \int_{f_0}^{f} P(f') df'.$$

A straight line (as indicated by the dotted line in the figure) connecting the maximum point and the minimum point of the curve $\phi(f)$ may be represented as:

$$C(f) = \int_{f_0}^{f} k df',$$

Wherein, k is the slope of the straight line $k=[\phi(f_1)-P(f_0)]/(f_1-f_0)$, $f_1$ is the forward frequency range.

If subtraction is performed on the two lines shown in FIG. 3(b), a curve $\phi(f)$ as shown in FIG. 3(c) can be obtained:

$$\phi'(f)=\phi(f)-C(f)$$

In the curve $\phi(f)$, the position corresponding to the maximum value is the estimated forward maximum frequency $f_{max+}$ and that corresponding to the minimum value is the estimated backward maximum frequency $f_{max-}$. The positions corresponding to the two vertical lines in FIG. 3 indicate the forward maximum frequency and backward maximum frequency obtained through initial estimation in this embodiment, which are equal to 49 and 10 Hz, respectively.

Most components of the Doppler signals are distributed between the estimated forward maximum frequency and the backward maximum frequency, while noise signals are distributed in the whole spectrum range, so the frequency components above the forward maximum frequency and below the backward maximum frequency are mainly the noise signals. As the above-mentioned drawbacks of MGM, it's apparent from FIG. 3 that the forward maximum frequency is underestimated. The step D of the invention thus uses the above signal distribution characteristics to estimate the average noise power more accurately, to correct the above initial estimation result.

The noise frequency range may be described as a function of the maximum frequency, and is expressed as:

$$[f_0, F(f_{max-})]+[F(f_{max+}), f_1].$$

where F(x) denotes a function of x, $[f_0, f_1]$ is the frequency range of the power spectrum P(f).

For simplicity, in this embodiment, assuming F(x)=x, and then the average noise power is expressed as:

$$E = \frac{\int_{f_0}^{fmax-} P(f)df + \int_{fmax+}^{f_1} P(f)df}{fmax- - f_0 + f_1 - fmax+}.$$

Afterwards, in order to utilize the average noise power E to correct the forward maximum frequency and the backward maximum frequency, a threshold Th(E) is set according to the average noise power E at the current moment and previous average noise powers E at previous moments. Since the estimated average noise power at each moment has some errors, the estimated average noise power at the current moment may be smoothed by using the previous average noise powers at previous moments, so as to reduce the errors of the average noise power E.

Accordingly, the threshold Th(E) may be represented as a function of the average noise power at the current moment and the previous average noise powers at previous moments, that is, Th(E)=F($E_t$, $E_{t-1}$, $E_{t-2}$, ... ), where $E_t$ is the average noise power at the current moment t and $E_{t-i}$ is the previous average noise power at a previous moment t−i. For simplicity, in this embodiment, the threshold may be assumed as Th(E)=a*E, that is, the threshold is a function of the average noise power only at the current moment t, where a>1 is an adjustable constant.

Next, the threshold is subtracted from the power spectrum P(f) of the Doppler signals at the predetermined moment, i.e., P(f)−Th(E), and the difference function is integrated:

$$\phi'' = \int_{f_0}^{f} [P(f') - Th(E)]df'$$
$$= \int_{f_0}^{f} P(f')df' - \int_{f_0}^{f} Th(E)df'$$
$$= \phi(f) - C'(f).$$

It can be seen from the function $\phi''(f)$ that this operation is very similar to MGM, except that the straight line represented by the second integral term of the function $\phi''(f)$ has a different slope. Specifically, in the function $\phi''(f)$, the slope of the line C'(f) (see FIG. 4(b)) is related to the average noise power only, but in MGM, the slope of the line C(f) is related to the average power about the signals and the noises. By increasing the adjustable index a, the line C'(f) approaches the line C(f) nearer and nearer, and the estimated maximum frequency also approximates the result of MGM gradually.

Figure 4:
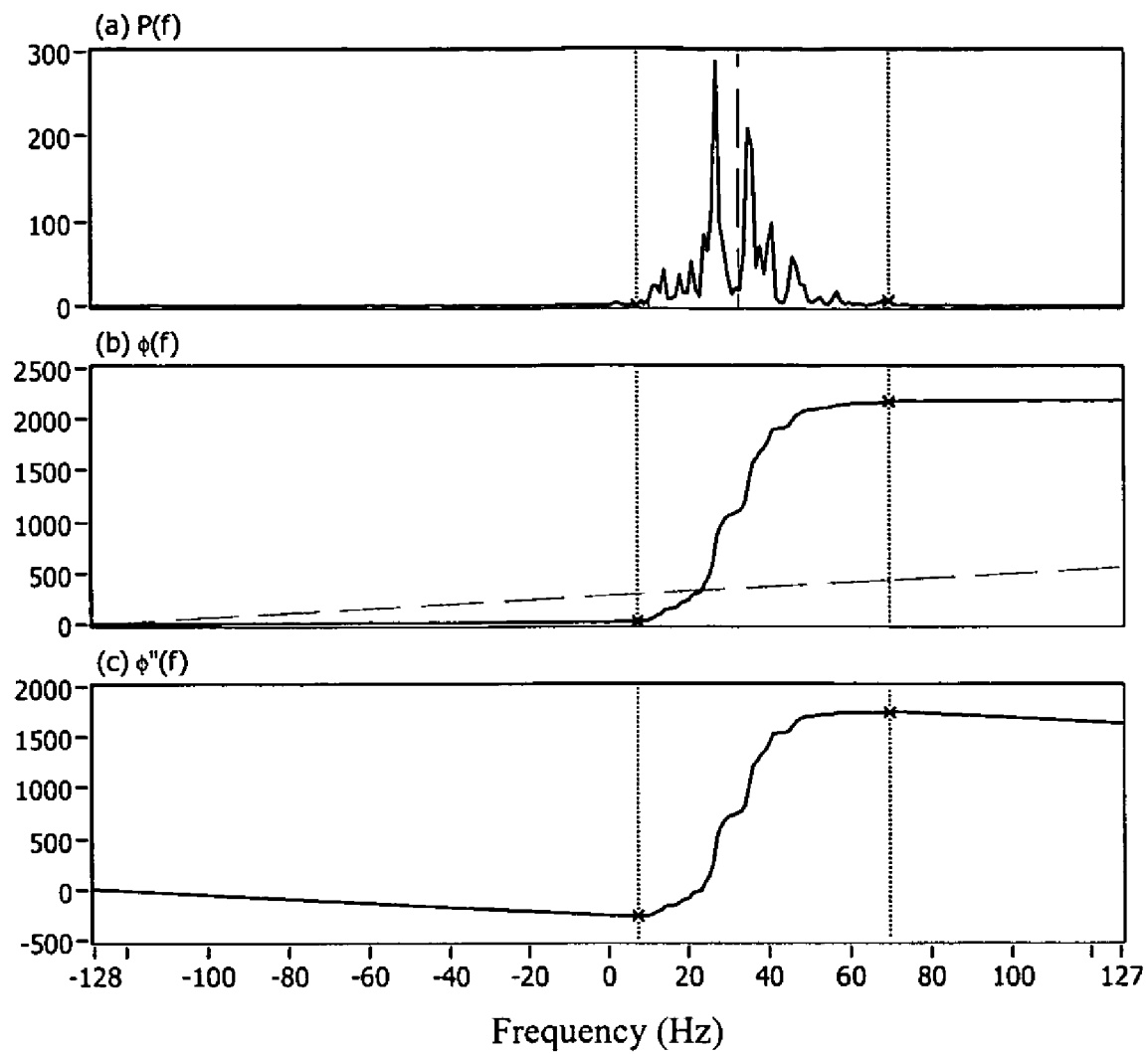
FIG. 4 is a schematic view showing the correction process for the estimation of the maximum frequency shown in FIG. 3.

The maximum and minimum values in the function $\phi''(f)$ are then searched for, and the positions for the maximum and minimum values correspond to the corrected forward maximum frequency $F_{max+}$ and the corrected backward maximum frequency $F_{max-}$, respectively. The result is shown in FIG. 4(c). The corrected forward maximum frequency $F_{max+}$ and backward maximum frequency $F_{max-}$ corresponding to the vertical dotted lines are equal to 70 and 7 Hz respectively. It can be seen from FIG. 4(a) that both of them have better estimation accuracy.

After the forward maximum frequency and the backward maximum frequency are corrected, the frequency range of the Doppler blood flow signals can be determined more precisely. The power spectrum components between the two envelope curves (that is, the frequency range between the corrected forward maximum frequency $F_{max+}$ and backward maximum frequency $F_{max-}$) may be used to estimate the mean frequency $F_{mean}$ of the signals. The computation by the first moment of the frequency for example, is given by:

$$F_{mean} = \frac{\int_{F_{max-}}^{F_{max+}} f * P(f) df}{\int_{F_{max-}}^{F_{max+}} P(f) d(f)}$$

Without impact from noises outside the range of the blood flow velocity, the mean frequency estimated by the above method has better accuracy. In this embodiment, the mean frequency is 32.6 Hz, and the vertical dotted lines in FIG. 4(a) depict the corresponding positions.

The method of the invention further comprises a step of determining the maximum frequency to be output according to the direction of the blood flow velocity, and has better robustness over the step of determining the maximum frequency by directly using the positions corresponding to the maximum power. Specifically, after quadrature demodulation, the in-phase and quadrature channels of the Doppler signals may be used for velocity direction detection of a bi-directional blood flow. In this embodiment, the frequency range below 0 Hz corresponds to a backward blood flow and that above 0 Hz corresponds to a forward blood flow. The power spectrum components between the corrected forward maximum frequency $F_{max+}$ and backward maximum frequency $F_{max-}$ are used to estimate the mean frequency $F_{mean}$. Then, the maximum frequency $F_{max}$ is finally determined according to the direction of the mean flow velocity corresponding to the mean frequency. In this embodiment, the mean frequency 32.6 Hz>0 Hz, thus it can be determined that the mean flow velocity is positive. Accordingly, the finally output maximum frequency $F_{max}$ is 70 Hz, that is, the corrected forward maximum frequency is selected to output as the maximum frequency.

Alternatively, the maximum frequency may be determined according to the integration values of the power spectra of the forward and backward blood flows. Integration is first performed on the power spectra corresponding to the forward and backward blood flows respectively. And then, determination is made based on the integration values, that is, if the integration value corresponding to the power spectrum of the forward blood flow is larger, the forward maximum frequency $F_{max+}$ is selected to output as the maximum frequency; otherwise, the backward maximum frequency $F_{max-}$ is selected to output as the maximum frequency.

After the maximum frequencies and the mean frequencies of power spectra at different moments are estimated, the points corresponding to the frequencies may be connected to form an envelope curve and then the envelope curve is displayed on the spectrogram. Due to influence from noises, the maximum frequency curve extracted with this method may have some errors, however the curve may be smoothed through linear or nonlinear digital filtering, so as to reduce the errors (which fall within prior arts and the description thereto is omitted).

Figure 5:
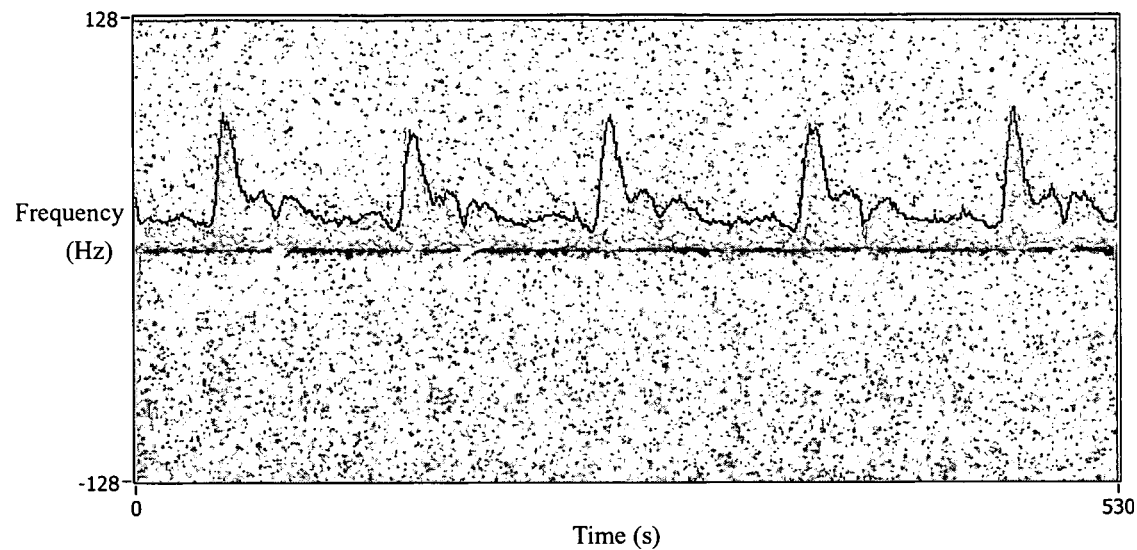
FIG. 5 is an example showing the estimation result for the maximum frequency in the spectrogram.
Figure 6:
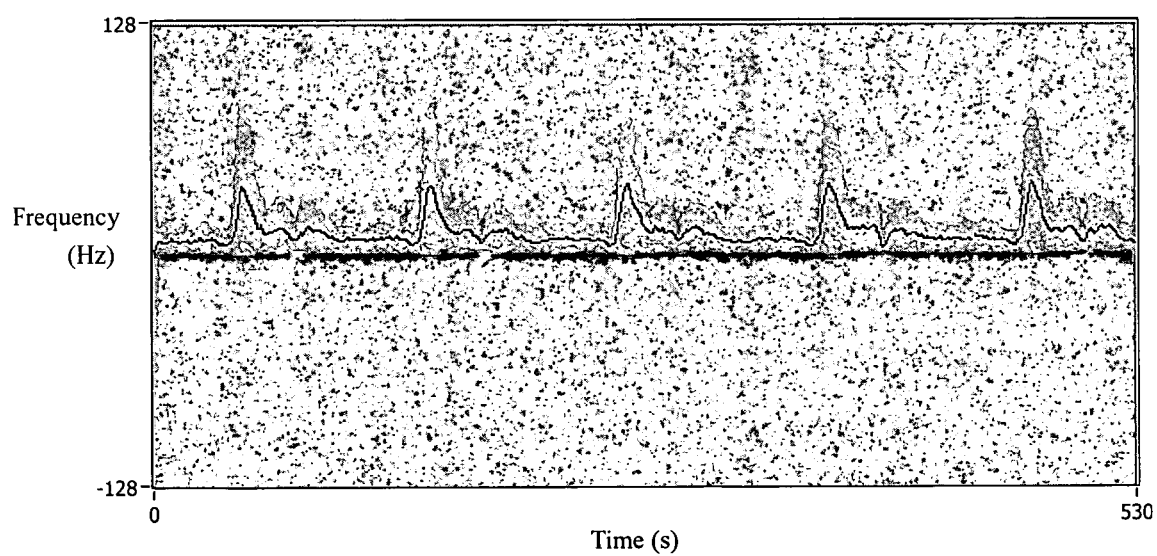
FIG. 6 is an example showing the obtained mean frequency curve.

The above technique is applicable for performing spectrum envelope extraction on carotid Doppler signals detected by the pulsed wave Doppler system and the results are shown in FIGS. 5 and 6. Wherein, the maximum frequency curve is indicated by the black curve in FIG. 5, the mean frequency curve is indicated by the black curve in FIG. 6. According to FIGS. 5 and 6, the maximum frequency curve and the mean frequency curve both track the spectrogram spectrum envelope very nicely. Furthermore, the mean frequency curve is very smooth and is not prone to influence from noises.

The method for extracting an envelope curve of a spectrogram according to the invention may be implemented in software or hardware. When the method for extracting an envelope curve of a spectrogram according to the invention is implemented in hardware, the apparatus for extracting an envelope curve of a spectrogram according to the invention comprises: a processing unit, for processing RF ultrasound echo signals to obtain Doppler signals; an analyzing unit, for performing spectral analysis on the Doppler signals, to obtain a power spectrum P(f) of the Doppler signals which varies over time; a frequency estimation unit, for estimating a forward maximum frequency $f_{max+}$ and a backward maximum frequency $f_{max-}$ for the Doppler signals at a predetermined moment, according to the power spectrum P(f) of the Doppler signals at the predetermined moment; a noise estimation unit, for determining a noise frequency range according to the forward maximum frequency and the backward maximum frequency, and estimating an average noise power E within the noise frequency range; and a correcting unit, for correcting the forward maximum frequency and the backward maximum frequency by using the average noise power E to obtain the corrected forward maximum frequency $F_{max+}$ and the corrected backward maximum frequency $F_{max-}$.

The correcting unit further comprises a threshold setting subunit, for setting a threshold Th(E) according to the average noise power E and previous average noise powers E at previous moments; a difference computation subunit, for subtracting the threshold set by the threshold setting subunit from the power spectrum P(f) of the Doppler signals at the predetermined moment to get a difference function P(f)-Th(E); and a frequency correction unit, for integrating the difference function to get a function ϕ"(f) and obtaining a maximum value and a minimum value of the function ϕ"(f), wherein positions of the maximum value and the minimum value corresponding to the corrected forward maximum frequency $F_{max+}$ and backward maximum frequency $F_{max-}$, respectively.

What is claimed is:

1. A method for extracting an envelope curve of a spectrogram, for use in measurement of blood flow velocity by using spectral Doppler techniques, comprising steps of:
   A. processing RF ultrasound echo signals to obtain Doppler signals;
   B. performing spectral analysis on the Doppler signals, to obtain a power spectrum P(f) of the Doppler signals which varies over time;
   C. estimating a forward maximum frequency $f_{max+}$ and a backward maximum frequency $f_{max-}$ for the Doppler signals at a predetermined moment, according to the power spectrum P(f) of the Doppler signals at the predetermined moment;
   D. determining a noise frequency range based on the estimated forward maximum frequency and the estimated backward maximum frequency, and estimating an average noise power E within the determined noise frequency range; and
   E. correcting the forward maximum frequency and the backward maximum frequency by using the average noise power E to obtain the corrected forward maximum frequency $F_{max+}$ and the corrected backward maximum frequency $F_{max-}$.

2. The method according to claim 1, wherein:
   the noise frequency range is a function of the forward maximum frequency and the backward maximum frequency, represented as $[f_0, F(f_{max-})]+[F(f_{max+}), f_1]$, where $F(f_{max-})$ is a function of variable $f_{max-}$, $F(f_{max+})$ is a function of variable $f_{max+}$ and $[f_0, f_1]$ is the frequency range of the power spectrum P(f).

3. The method according to claim 1, wherein the step E further comprises steps of:
   a. setting a threshold Th(E) according to the average noise power E and previous average noise powers E at previous moments;
   b. subtracting the threshold from the power spectrum P(f) of the Doppler signals at the predetermined moment to get a difference function P(f)-Th(E); and
   c. integrating the difference function to get a function Ø"(f) and obtaining a maximum value and a minimum value of the function Ø"(f), wherein positions of the maximum value and the minimum value corresponding to the corrected forward maximum frequency $F_{max+}$ and backward maximum frequency $F_{max-}$, respectively.

4. The method according to claim 3, wherein:
   the threshold Th(E) is represented as a function of the average noise power and the previous average noise powers at previous moments, that is, $Th(E)=F(E_t, E_{t-1}, E_{t-2}, \ldots)$, wherein $E_t$ is the average noise power and $E_{t-i}(i=1, 2, \ldots)$ is the previous average noise power at a previous moment t−i.

5. The method according to claim 1, wherein the step E is followed by the step of:
   F. determining one of the corrected forward maximum frequency $F_{max+}$ and the corrected backward maximum frequency $F_{max-}$ as the maximum frequency according to the direction of the blood flow velocity.

6. The method according to claim 5, wherein the step F further comprises:
   estimating an average frequency according to the frequency components between the corrected forward maximum frequency $F_{max+}$ and the corrected backward maximum frequency $F_{max-}$;
   determining the direction of the blood flow velocity corresponding to the average frequency; and
   determining one of the corrected forward maximum frequency $F_{max+}$ and the corrected backward maximum frequency $F_{max-}$ as the maximum frequency according to the determined direction of the blood flow velocity.

7. The method according to claim 5, wherein the step F further comprises:
   determining one of the corrected forward maximum frequency $F_{max+}$ and the corrected backward maximum frequency $F_{max-}$ as the maximum frequency according to the integration values of the power spectrums for the forward and backward blood flow in the power spectrum of the Doppler signals at the predetermined moment.

8. The method according to claim 5, wherein:
   errors for the maximum frequency are reduced further through linear or nonlinear smooth filtering.

9. The method according to claim 6, wherein:
   errors for the maximum frequency are reduced further through linear or nonlinear smooth filtering.

10. The method according to claim 7, wherein:
    errors for the maximum frequency are reduced further through linear or nonlinear smooth filtering.

11. The method according to claim 5, wherein the step F further comprises:
    fitting the maximum frequencies at different moments to get an envelope curve; and
    displaying the envelope curve on the spectrogram.

12. The method according to claim 6, wherein the step F further comprises:
    fitting the maximum frequencies at different moments to get an envelope curve; and
    displaying the envelope curve on the spectrogram.

13. The method according to claim 7, wherein the step F further comprises:
fitting the maximum frequencies at different moments to get an envelope curve; and
displaying the envelope curve on the spectrogram.

14. An apparatus for extracting an envelope curve of a spectrogram, for use in measurement of blood flow velocity by using spectral Doppler techniques, the apparatus comprising:
a processing unit configured to process RF ultrasound echo signals to obtain Doppler signals;
an analyzing unit configured to perform spectral analysis on the Doppler signals to obtain power spectrum P(f) of the Doppler signals which varies over time;
a frequency estimation unit configured to estimate a forward maximum frequency $f_{max+}$ and a backward maximum frequency $f_{max-}$ for the Doppler signals at a predetermined moment according to the power spectrum P(f) of the Doppler signals at the predetermined moment;
a noise estimation unit configured to determine a noise frequency range based on the estimated forward maximum frequency and the estimated backward maximum frequency, and to estimate an average noise power E within the determined noise frequency range; and
a correcting unit configured to correct the forward maximum frequency and the backward maximum frequency by using the average noise power E to obtain the corrected forward maximum frequency $F_{max+}$ and the corrected backward maximum frequency $F_{max-}$.

15. The apparatus according to claim 14, wherein the noise estimation unit is further configured to estimate the noise frequency range as a function of the forward maximum frequency and the backward maximum frequency, represented as $[f_0, F(f_{max-})]+[F(f_{max+}), f_1]$, wherein $F(f_{max-})$ is a function of variable $f_{max-}$, $F(f_{max+})$ is a function of variable $f_{max+}$ and $[f_0, f_1]$ is the frequency range of the power spectrum P(f).

16. The apparatus according to claim 14, wherein the correcting unit further comprises:
a threshold setting subunit configured to set a threshold Th(E) according to the average noise power E and previous average noise powers E at previous moments;
a difference computation subunit configured to subtract the threshold from the power spectrum P(f) of the Doppler signals at the predetermined moment to get a difference function P(t)−Th(E); and
a frequency correction subunit configured to integrate the difference function to get a function $Ø''(f)$ and to obtain a maximum value and a minimum value of the function $Ø''(f)$, wherein positions of the maximum value and the minimum value correspond to the corrected forward maximum frequency $F_{max+}$ and backward maximum frequency $F_{max-}$, respectively.

* * * * *

UNITED STATES PATENT AND TRADEMARK OFFICE
CERTIFICATE OF CORRECTION

PATENT NO.        : 7,611,467 B2                                         Page 1 of 1
APPLICATION NO.   : 11/316048
DATED             : November 3, 2009
INVENTOR(S)       : Yu Zhang It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 878 days.

Signed and Sealed this

Twelfth Day of October, 2010

David J. Kappos
*Director of the United States Patent and Trademark Office*